United States Patent
Fladoos

(10) Patent No.: US 10,342,889 B1
(45) Date of Patent: Jul. 9, 2019

(54) ELECTRICALLY ACTUATED ADHESIVE PHYSIO TAPE WITH THERMAL PROPERTIES

(71) Applicant: Jason Fladoos, Santa Monica, CA (US)

(72) Inventor: Jason Fladoos, Santa Monica, CA (US)

( * ) Notice: Subject to any disclaimer, the term of this patent is extended or adjusted under 35 U.S.C. 154(b) by 0 days.

(21) Appl. No.: 16/184,188

(22) Filed: Nov. 8, 2018

Related U.S. Application Data

(63) Continuation-in-part of application No. 16/120,651, filed on Sep. 4, 2018, which is a continuation-in-part of application No. 16/022,569, filed on Jun. 28, 2018.

(51) Int. Cl.
| | | |
|---|---|---|
| A61F 7/00 | (2006.01) | |
| A61F 13/02 | (2006.01) | |
| A61L 15/14 | (2006.01) | |
| A61F 5/01 | (2006.01) | |
| A61L 15/12 | (2006.01) | |
| H01R 25/16 | (2006.01) | |

(52) U.S. Cl.
CPC ............ *A61L 15/14* (2013.01); *A61F 5/0104* (2013.01); *A61F 7/007* (2013.01); *A61L 15/12* (2013.01); *A61F 2007/0093* (2013.01); *H01R 25/162* (2013.01)

(58) Field of Classification Search
None
See application file for complete search history.

(56) References Cited

U.S. PATENT DOCUMENTS

| | | | |
|---|---|---|---|
| 2,573,791 A | 11/1951 | Howells | A61F 7/03 |
| | | | 126/263.02 |
| 5,431,622 A | 7/1995 | Pyrozyk | A61F 13/0203 |
| | | | 602/2 |
| 7,621,110 B2 | 11/2009 | Ota | A61F 7/034 |
| | | | 126/263.02 |

(Continued)

FOREIGN PATENT DOCUMENTS

WO   WO-2015156794 A1 * 10/2015 ............... F25B 9/145

OTHER PUBLICATIONS

Rujun Ma et al., Highly Efficient Electrocaloric Cooling With Electrostatic Actuation, published Sep. 15, 2017 in Science 357 (6356), 1130-1134.

*Primary Examiner* — Kim M Lewis
(74) *Attorney, Agent, or Firm* — William J. Benman; Benman, Brown & Williams

(57) ABSTRACT

A flexible adhesive kinesiology or physio tape adapted to provide heating as well as cooling in response to an electrical signal. In a general illustrative embodiment, the inventive tape includes a first layer of flexible high quality porous fabric; a pad of electrocaloric polymeric material mounted on the layer of porous fabric; and a controller, mounted on the tape, for electrically actuating the pad of electrocaloric material. In the best mode, plural pads of polarized electrocaloric polymer film are provided with nanotube electrodes mounted therebetween. The first layer of porous fabric includes plural arrangements for retaining the plural pads and providing male and female electrical connections (Continued)

thereto. A bus is mounted on the first layer for providing electrical connection between the controller and the electrical connections to the pads of film. In the best mode, a second layer of porous fabric is included to sandwich the pads between the first layer of porous fabric and the second layer of porous fabric.

19 Claims, 4 Drawing Sheets

(56) References Cited

U.S. PATENT DOCUMENTS

| | | | |
|---|---|---|---|
| 9,681,994 B2* | 6/2017 | Case-Gustafson | A61F 13/15203 |
| 2006/0002988 A1 | 1/2006 | Ellefson | A61F 13/00063 424/448 |
| 2006/0282138 A1 | 12/2006 | Ota | A61F 7/03 607/96 |
| 2008/0147153 A1 | 6/2008 | Quincy | A61F 7/03 607/114 |
| 2010/0234785 A1 | 9/2010 | Liebowitz | A61F 5/0118 602/61 |
| 2010/0241089 A1 | 9/2010 | Uchiyama | A61F 7/034 604/291 |
| 2014/0057192 A1* | 2/2014 | Ohno | H01M 4/8626 429/444 |
| 2014/0230453 A1* | 8/2014 | Kruglick | F25B 21/00 62/3.1 |
| 2014/0243940 A1 | 8/2014 | Schuller | A61F 7/106 607/110 |
| 2014/0257155 A1 | 9/2014 | Altinok | A61H 39/04 602/1 |
| 2014/0308338 A1 | 10/2014 | Nierle | A61F 13/025 424/448 |
| 2014/0316355 A1 | 10/2014 | Lim | A61K 9/7084 604/291 |
| 2015/0328054 A1 | 11/2015 | Capobianco | A61F 13/0236 602/46 |
| 2016/0106595 A1* | 4/2016 | Arbesman | A61F 13/00059 602/54 |
| 2016/0128950 A1* | 5/2016 | Mitroo | A61K 36/79 604/290 |
| 2016/0309808 A1* | 10/2016 | Armour | A41D 13/0512 |
| 2017/0056252 A1* | 3/2017 | Arbesman | A61F 13/107 |
| 2017/0240777 A1* | 8/2017 | Proctor, Jr. | A61L 15/58 |
| 2017/0360542 A1* | 12/2017 | Brasch | A61F 13/0269 |
| 2018/0010019 A1* | 1/2018 | Han | C09J 133/06 |
| 2018/0042775 A1* | 2/2018 | Kendrick | A61L 15/26 |
| 2018/0289530 A1* | 10/2018 | van den Dries | A61F 13/02 |

* cited by examiner

1. A two-layer EC polymer stack with CNT electrodes

2. EC device architecture

KNOWN ART

ELECTRICALLY ACTUATED ADHESIVE PHYSIO TAPE WITH THERMAL PROPERTIES

BACKGROUND OF THE INVENTION

Field of the Invention

The present invention relates to tapes and bindings. More specifically, the present invention relates to therapeutic physio and kinesiology tapes and bindings.

Description of the Related Art

Physio tape (aka kinesiology tape) is a tape that is used for treating athletic injuries and a variety of physical disorders. Physio tape is conventionally a thin, stretchy, elastic cotton strip with an acrylic adhesive. Therapeutic physio tape can be used to treat inflammation as well as a wide variety of musculoskeletal and sports injuries. Physio tape may be manufactured to emulate human skin in both thickness and elasticity to allow the tape to be worn without binding, constriction or restriction of movement.

Physio tapes generally provide support. However, therapists are likely to appreciate that there is a need in the art for a tape that provides support as well as thermal properties such as heat and cold.

SUMMARY OF THE INVENTION

The need in the art is addressed by the flexible adhesive kinesiology or physio tape of the present invention adapted to provide heating as well as cooling in response to an electrical signal. In a general illustrative embodiment, the inventive tape includes a first layer of flexible high quality porous fabric; a pad of electrocaloric polymeric material mounted on the layer of porous fabric; and a controller, mounted on the tape, for electrically actuating the pad of electrocaloric material.

In the best mode, plural pads of polarized electrocaloric poly (vinylidene fluoride-ter-trifluoroethylene-ter-chlorofluoroethylene) polymer film are provided with nanotube electrodes mounted therebetween. The first layer of porous fabric includes plural arrangements for retaining the plural pads and providing male and female electrical connections thereto. A bus is mounted on the first layer for providing electrical connection between the controller and the electrical connections to the pads of film. In the best mode, a second layer of porous fabric is included to sandwich the pads between the first layer of porous fabric and the second layer of porous fabric.

DESCRIPTION OF THE INVENTION

Illustrative embodiments and exemplary applications will now be described with reference to the accompanying drawings to disclose the advantageous teachings of the present invention.

While the present invention is described herein with reference to illustrative embodiments for particular applications, it should be understood that the invention is not limited thereto. Those having ordinary skill in the art and access to the teachings provided herein will recognize additional modifications, applications, and embodiments within the scope thereof and additional fields in which the present invention would be of significant utility.

Figure 1:
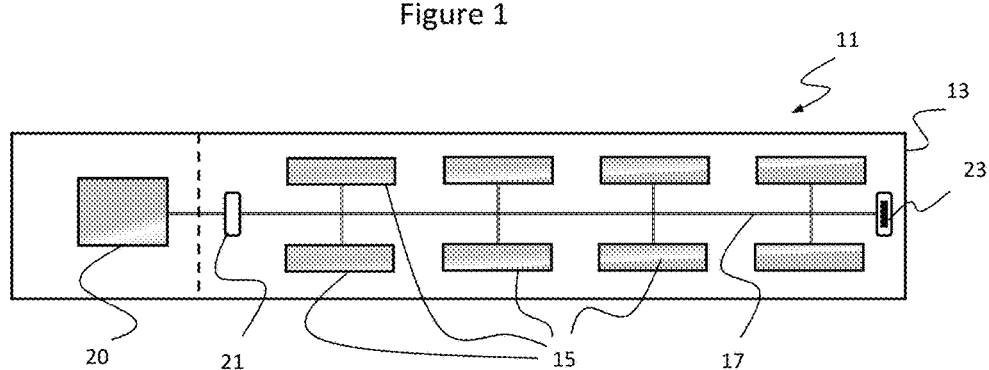
FIG. 1 is a top view of an illustrative embodiment of the tape of the present invention with the upper layer removed for clarity.

FIG. 1 is a top view of an illustrative embodiment of the tape of the present invention with the upper layer removed for clarity. In a general illustrative embodiment, the inventive tape 11 includes a first (base) layer 13 of flexible fabric such as is currently used for adhesive physio tape. That is, the base layer 13 may be fabricated by applying a strong adhesive such as zinc oxide or other suitable adhesive to a large sheet of high quality porous fabric such as a blend of cotton, latex and/or nylon. In the illustrative embodiment, the tape has a width of 1-4 inches, a thickness of 1-5 mm and a length of 6 inches to any length.

In accordance with the present teachings, to effectuate heating and cooling electrically, the inventive physio tape 11 includes plural pads or stacks 15 of electrocaloric polymeric material mounted on the base layer 13. The design and operation of the pads are discussed more fully below. The pads 15 are connected to a controller 20 via a bus 17 and a male/female connector 21. As shown by the dotted line in FIG. 1, the controller 20 may be mounted on the base layer 13 or on a separate module.

Figure 2:
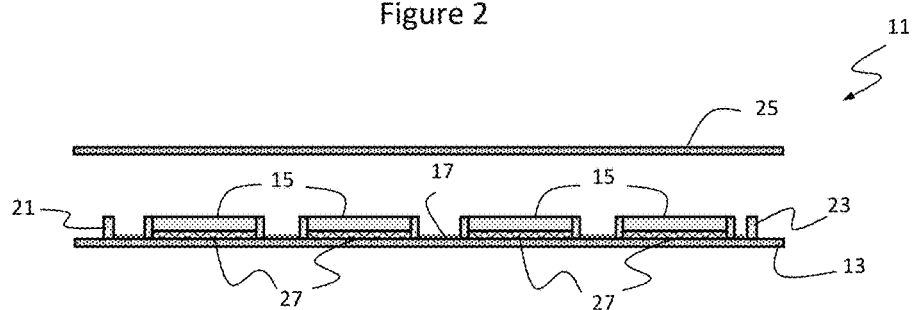
FIG. 2 is a side view of the tape of FIG. 1 with the second layer thereof partially disassembled therefrom.

FIG. 2 is a side view of the tape of FIG. 1 with a second layer 25 shown partially disassembled therefrom.

Figure 3:
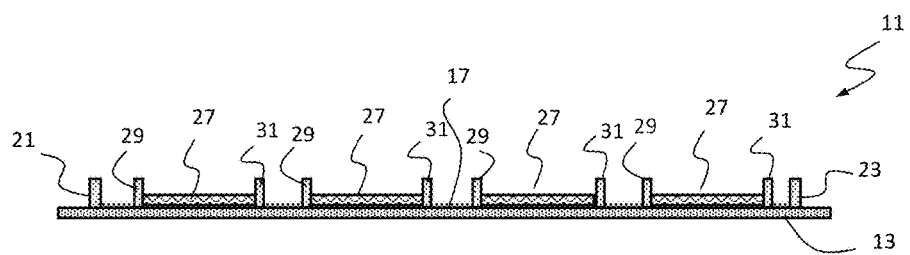
FIG. 3 shows the side view of FIG. 2 with the second porous layer and the electrocaloric pads thereof removed for clarity.

FIG. 3 shows the side view of FIG. 2 with the second porous layer and the electrocaloric pads thereof removed for clarity.

Figure 4:
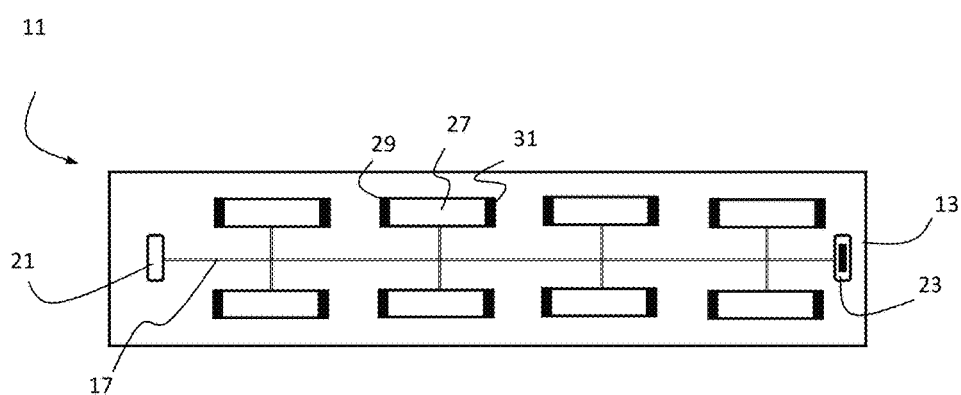
FIG. 4 is a top view of the tape depicted in FIG. 3.

FIG. 4 is a top view of the tape depicted in FIG. 3.

Figure 5:
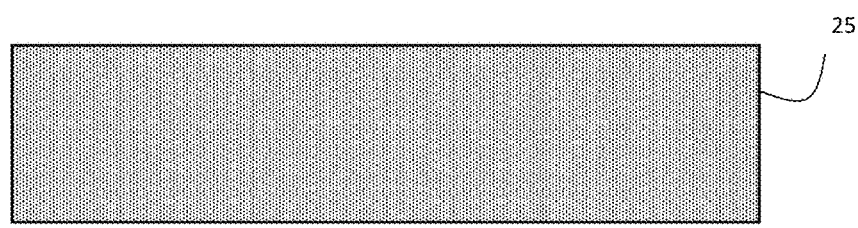
FIG. 5 is a top view of the second layer of the tape shown in FIG. 2.

FIG. 5 is a top view of the second layer of the tape shown in FIG. 2. As shown in FIG. 5, in the best mode, a second layer of porous fabric 25 is included to sandwich the pads between the first layer of porous fabric and a second layer of porous fabric.

As shown in FIGS. 2-5, the pads 15 are retained and electrically coupled to the bus 17 by 29 and 31. A layer of adhesive 27 is provided to retain the pads 15 between the connecting elements 29 and 31. As an alternative, the adhesive layers 27 are replaced with magnets which double as heat sources or heat sinks as discussed more fully below. If the magnets are used, a magnetic shield should be included to avoid interference with the electrostatic operation of the pads.

In the best mode, the pads are implemented in accordance with the teachings of a paper entitled *Highly Efficient Electrocaloric Cooling With Electrostatic Actuation* by Rujun Ma, Ziyang Zhang, Kwing Tong, David Huber, Roy Kornbluh, Yongho Sungtaek Ju, Qibing Pei published Sep. 15, 2017 in Science 357 (6356), 1130-1134.

Figure 6:
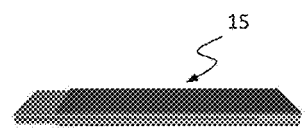
FIG. 6 is a side perspective view of a two-layer electrocaloric polymer stack with carbon nanotube electrodes in accordance with conventional teachings.

FIG. 6 is a side perspective view of a two-layer electrocaloric polymer stack with carbon nanotube electrodes in accordance with such teachings.

Figure 7:
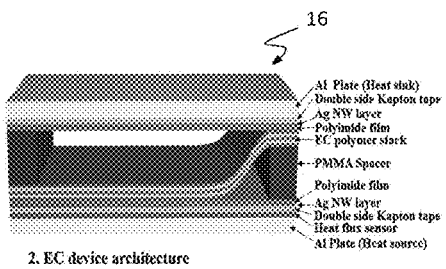
FIG. 7 is a side perspective view of a two-layer electrocaloric polymer stack with carbon nanotube electrodes of FIG. 6 with heat sinks, spacers and heat flux sensor in accordance with conventional teachings.

FIG. 7 is a side perspective view of a two-layer electrocaloric polymer stack 16 with carbon nanotube electrodes of FIG. 6 with heat sinks, spacers and heat flux sensor in accordance with conventional teachings.

In the above-noted paper, Ma et al. disclosed an electrocaloric (EC) refrigeration-device architecture (FIG. 6) where they used electrostatic actuation to rapidly transport a flexible EC polymer stack between a heat source and a heat sink. The electrostatic force not only moved the EC material but also promoted the formation of intimate thermal contact between the EC polymer stack and the heat source and heat sink during each cycle. They developed a compact solid-state cooling device (FIGS. 6 and 7) 7 cm by 3 cm by 0.6 cm with a COP of 13 at a heat flux of 29.7 mW/cm2 and a specific cooling power of 2.8 W/g, which is higher than other magnetocaloric, elastocaloric (17-26), and thermoelectric devices.

The EC device offered a much better performance than the large-scale magnetocaloric refrigerator, which has a COP of 1.9 and a specific cooling power of 2 W/g (17). Further, the thin-film EC cooling device is flexible and can conform to surfaces with complex curvature. The device also operated without the noise and complexity of a conventional cooling system.

They selected poly (vinylidene fluoride-ter-trifluoroethylene-ter-chlorofluoroethylene) P(VDF-TrFE-CFE) as the active EC material because of its large entropy change, large $\Delta T$ near room temperature, and mechanical flexibility. They used single-walled carbon nanotubes (CNTs) to form the electrodes of the EC film because of their mechanical compliance, thermal stability, and oxidation resistance. They drop-cast the P(VDF-TrFE-CFE) solution onto a glass substrate, and the resulting polymer film was heated at 90° C. They spray-coated a dispersion of CNTs in an isopropyl alcohol and water mixture onto the polymer film. They laminated one of the as-prepared films directly to the top of another, with one CNT layer sandwiched between the EC films. The overlap of the CNT areas (areas with electrodes on both sides of the film) defined the active area (2 cm by 5 cm) for the EC effect. They also spray-coated the bottom surface of the stack with CNTs to complete the fabrication of a two-layer EC polymer stack (FIG. 6). They then placed the EC laminate in a vacuum oven at 120° C. for 16 hours to remove the residual solvent, raise the degree of crystallinity, and enhance the polarizability of the polymer (29). The total mass of the EC laminate was 0.23 g.

Their EC cooling device comprised two laminated sheets 7 cm by 3 cm in area and separated by a 6-mm-thick spacer made of poly(methyl methacrylate). Each laminate sheet consisted of a double-sided Kapton tape, a polyimide film, and a silver-nanowire percolation network layer inserted in between. The nanowire percolation layer acted as one electrode of the electrostatic actuator. They mounted the EC polymer stack on one end of the EC device between the left spacer and the lower laminate sheet, and the other end between the right spacer and the upper laminate sheet (FIGS. 6 and 7). For testing convenience, They attached a 6.3-mm-thick aluminum plate to the outer sticky surface of each of the Kapton tape layers. The bottom and top plates acted as the heat source and heat sink, respectively. They inserted a heat flux sensor composed of a thermopile of thermocouples across a polyimide sheet [OMEGA heat flux sensor HFS-4, 2.06 mV/(W/m2)] between the aluminum plate heat source and the Kapton tape for in situ thermal measurement. The cross-sectional view of the EC polymer stack shows that it forms an S shape. The stationary ends of the S-shaped film allow the film to make good thermal contact with the electrodes of the top or bottom aluminum plate.

During operation, the S-shaped EC film moves up and down like a flexure spring, driven by electrostatic forces when a voltage is applied between one of the silver-nanowire layers and the corresponding outer CNT layer on the EC stack that faces the silver-nanowire layer. Because of its light weight and low bending stiffness, the EC stack could be shuttled rapidly between attachment to the upper and lower laminates with a response time of less than 30 ms and total energy consumption of only ~0.02 W.

This electrostatic actuation is reported as compact, noiseless, and does not incur substantial frictional forces that could induce material damage and cause energy consumption, and thus parasitic heating. The instantaneous (adiabatic) temperature increase of the EC stack when an electric field is applied results from the dipole orientation in the relaxor ferro-electric polymer and consequent decrease of entropy in the system.

The actuation of the polymer stack was achieved by applying an electrostatic field across the polyimide film of either the bottom or top plate to drive the movement of the EC polymer stack. See FIGS. 8a-9d.

Figure 8B:
FIG. 8b is a series of diagrams that illustrate a change in entropy of the stack of FIG. 8a in response to the application of electrical potential thereto.
Figure 8A:
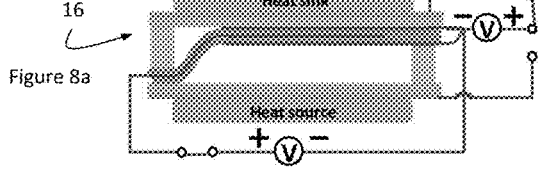
FIG. 8a is an electrical schematic diagram that illustrates the operation of an electrocaloric polymer tape of FIG. 6 in a first state thereof by which the polymer stack is actuated into contact with the heat sink thereof.

FIG. 8a is an electrical schematic diagram that illustrates the operation of an electrocaloric polymer tape of FIG. 6 in a first state thereof by which the polymer stack is actuated into contact with the heat sink thereof.

FIG. 8b is a series of diagrams that illustrate a change in entropy of the stack of FIG. 8a in response to the application of electrical potential thereto.

Figure 8D:
FIG. 8d is a series of diagrams that illustrate a change in entropy of the stack of FIG. 8c in response to the application of electrical potential thereto.
Figure 8C:
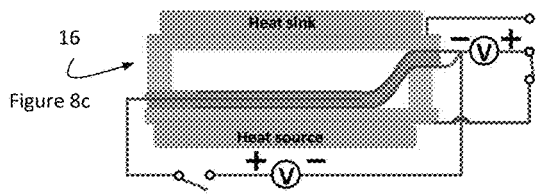
FIG. 8c is an electrical schematic diagram that illustrates the operation of an electrocaloric polymer tape of FIG. 6 in a second state thereof by which the polymer stack is actuated into contact with the heat source thereof.

FIG. 8c is an electrical schematic diagram that illustrates the operation of an electrocaloric polymer tape of FIG. 6 in a second state thereof by which the polymer stack is actuated into contact with the heat source thereof.

FIG. 8d is a series of diagrams that illustrate a change in entropy of the stack of FIG. 8c in response to the application of electrical potential thereto.

Figure 9A:
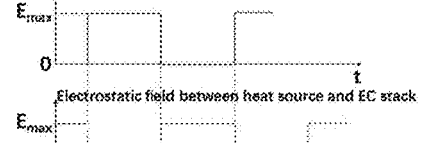
FIG. 9a is a diagram of the electrostatic field between the heat sink and the stack of FIG. 8a in the first state.

FIG. 9a is a diagram of the electrostatic field between the heat sink and the stack of FIG. 8a in the first state.

Figure 9B:
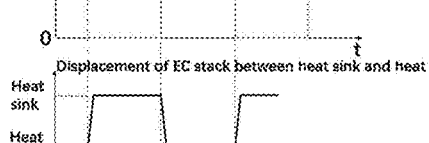
FIG. 9b is a diagram of the electrostatic field between the heat source and the stack of FIG. 8c in the second state.

FIG. 9b is a diagram of the electrostatic field between the heat source and the stack of FIG. 8c in the second state.

Figure 9C:
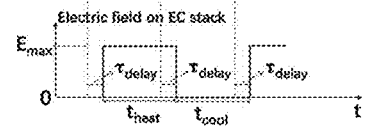
FIG. 9c is a diagram that illustrates the displacement of the stack of FIG. 6 between the first and second states.

FIG. 9c is a diagram that illustrates the displacement of the stack of FIG. 6 between the first and second states.

Figure 9D:
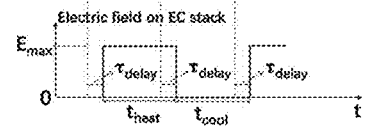
FIG. 9d is a timing diagram of the electric field on the stack of FIG. 6 between the first and second cool and heat states thereof.

FIG. 9d is a timing diagram of the electric field on the stack of FIG. 6 between the first and second cool and heat states thereof.

As illustrated in FIGS. 8a-9d, the electric field across the air gap determines the electrostatic force that acts to move the EC polymer stack. The electrostatic forces also determine the pressure between the EC film and the heat source and heat sink. Away from the attachment point, the pressure is dominated by the air gap. The air gap is largest at the point where the film attaches to the opposite electrode.

This approach to electrostatic actuation may be used when the bending stiffness of the film can be overcome by the electrostatic forces. The shape of the edge of the film gives this type of actuator the name "S-shaped film actuator" (30). Such electrostatic actuation has been used to move films for valving.

When an electric field is alternately applied across the top silver-nanowire electrode and the top CNT layer of the EC stack and the bottom silver-nanowire electrode and the bottom CNT layer of the EC stack, the EC polymer stack shuttles between the two aluminum plates. The electrostatic pressure on the film increases the thermal contact between the EC-stack film and polyimide and thus facilitates the heat flux between the EC material and the aluminum plates.

The operating cycle consists of six steps: (i) electrostatic actuation of the EC polymer stack toward the top aluminum plate (heat sink); (ii) electrocaloric heating of the EC polymer stack; (iii) heat transfer from the EC polymer stack to the heat sink; (iv) electrostatic actuation of the EC polymer stack toward the bottom aluminum plate (heat source); (v) electrocaloric cooling of the EC polymer stack; and (vi) heat transfer from the heat source to the EC polymer stack.

For simplicity of circuitry design, they fabricated the EC cooling device with a common cathode by connecting the two outer CNT electrodes of the EC polymer stack with a thin copper wire. The inner (middle) CNT electrode of the EC polymer stack serves as the anode to apply an electric field across the P(VDF-TrFE-CFE) film for electrocaloric heating. The silver-nanowire films function as the anode to apply an electrostatic field across the polyimide for electrostatic actuation. They controlled the voltage switching for electrostatic actuation by an electric relay to switch between the silver nanowire anodes of the heat source and heat sink.

During one cycle of heat transfer, an electrostatic field is first applied between the silver nanowire on the heat sink and the outer CNT electrodes to generate an electrostatic pressure to transport the EC polymer stack toward the heat sink. The time required to move the EC polymer stack from the heat source to the heat sink was roughly 0.03 s, but a short delay $t_{delay}$=0.15 s) was preprogrammed in the EC waveform to allow for the EC polymer stack to form sufficient thermal contact with the polyimide before applying an electric field across the P(VDF-TrFE-CFE) film. When an electric field is applied across the P(VDF-TrFE-CFE) film for electrocaloric heating, and the molecular dipoles become aligned, the resulting decrease in entropy increases the temperature of the EC polymer film. A temperature gradient is thus created, causing heat to be transferred from the EC polymer stack to the heat sink.

After a predefined time of heating, $t_{heat}$, the electrostatic actuation is switched by using the electric relay to transport the EC polymer film toward the heat source. After another short delay, $t_{delay}$, electrocaloric cooling occurs by switching off the electric field across the P(VDF-TrFE-CFE) film to allow for the dipoles within the polymer to become randomly aligned. The entropy of the film increases while heat is transferred from the heat source to the EC polymer stack during a predefined time of cooling, $t_{cool}$, thus completing one cycle of heat transfer.

They identified approaches that can further improve the performance of their device. When the aluminum heat sink and heat source were replaced by carbon nanotube-coated polyethylene terephthalate (PET) films (thickness of 100 mm), the temperature span was increased to 2.8 K.

In addition, they noted that, given the dielectric nature of EC polymer, energy recovery is possible during the depolarization process, which would further enhance the efficiency. The specific cooling power and COP puts this device in a different operational space when compared to elastocaloric, magnetocaloric, and thermoelectric devices reported in the literature.

They demonstrated the benefits of the inherent thinness and flexibility of their cooling device by fabricating a version that can conform to a nonflat surface. The P(VDF-TrFE-CFE) cooling device consisted of a transparent flexible frame made of conductive CNTs coated on a 100-mm-thick PET film that served as the laminate sheet for electrostatic actuation. They fixed the S-shaped EC polymer stack to a polydimethylsiloxane 4-mm-thick frame spacer. The device size was 7 cm by 3 cm by 0.5 cm.

Figure 10:
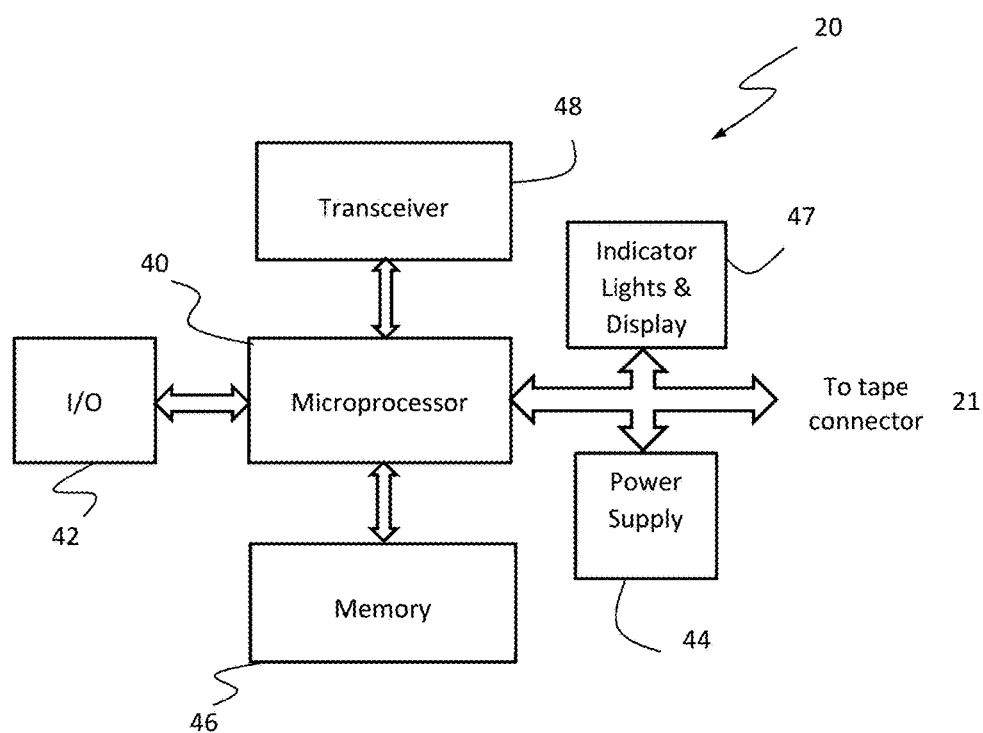
FIG. 10 is a block diagram of the electrical system utilized in connection with the electro-actuated heating and cooling physio tape of the present invention.

FIG. 10 is a block diagram of the electrical system utilized in connection with the electro-actuated heating and cooling physio tape of the present invention. As shown in FIG. 10, the controller 20 includes a microprocessor 40 coupled to a user interface 42 and programmed via software stored in memory 46 to regulate power to the pads 15 from a power supply and regulator 44 via the connector 21 and bus 17. Optional indicator lights and/or display 47 are included along with a wireless transceiver 48.

The present invention further includes an arrangement for providing for solar charging. This can be implemented with solar cells in a separate device coupled to the inventive tape via one or more wires. The solar cells may be used to charge a power source such as a battery, capacitor, etc.

Hence, an electrically actuated physio tape is disclosed for heating and cooling applications. Those having ordinary skill in the art and access to the present teachings will recognize additional modifications, applications and embodiments within the scope thereof. For example, a heating only embodiment may be implemented, in the alternative, with a plurality of conductive wires, embedded in or on the tape, that generate thermal energy when supplied with electrical current as is commonly used in heating blankets. The wires would be insulated, mounted along the length of the tape and may need to be coiled for stretchability. This simpler system that may prove to be much more cost effective for manufacturing purposes.

It is therefore intended by the appended claims to cover any and all such applications, modifications and embodiments within the scope of the present invention.

The invention claimed is:

1. A flexible adhesive kinesiology or physio tape adapted to provide heating and cooling, said tape comprising:
   a first layer of flexible high quality porous fabric;

a pad of electrocaloric polymeric material mounted on the flexible high quality layer of porous fabric; and a controller, mounted on said tape, for electrically actuating said pad of electrocaloric polymeric material.

2. The tape of claim 1 wherein said pad of electrocaloric polymeric material includes two layers of electrocaloric polymer film.

3. The tape of claim 2 wherein said polymer film is vinylidene fluoride-ter-trifluoroethylene-ter-chlorofluoroethylene.

4. The tape of claim 2 wherein said polymer film is polarized.

5. The tape of claim 4 wherein said pad includes a nanotube electrode mounted between said two layers of electrocaloric polymer film.

6. The tape of claim 1 further including plural pads of electrocaloric polymeric material mounted on said first layer of flexible high quality porous fabric.

7. The tape of claim 6 wherein said first layer of flexible high quality porous fabric includes plural arrangements for retaining said plural pads and providing electrical connections thereto.

8. The tape of claim 7 further including a bus mounted on said first layer of flexible high quality porous fabric for providing electrical connection between said controller and said electrical connections.

9. The tape of claim 8 further including male and female connectors coupled to said bus.

10. The tape of claim 1 further including male and female connectors mounted on said first layer for coupling a second layer to said first layer of flexible high quality porous fabric.

11. The tape of claim 1 further including a mechanism for retaining said pad to said first layer of flexible high quality porous fabric.

12. The tape of claim 1 further including a second layer of porous fabric mounted to sandwich said pad between said first layer of flexible high quality porous fabric and said second layer of porous fabric.

13. The tape of claim 1 wherein said controller includes a microprocessor.

14. The tape of claim 13 wherein said controller includes a power supply coupled to said microprocessor and said pad.

15. The tape of claim 14 wherein said controller includes a memory fixed in a tangible medium coupled to said microprocessor.

16. The tape of claim 15 wherein said controller further includes a user interface coupled to said microprocessor.

17. The tape of claim 16 wherein said memory includes software for effectuating actuation of the pad to provide heating or cooling in response to input from the user.

18. The tape of claim 16 wherein said controller further includes a wireless transceiver coupled to said microprocessor.

19. A flexible adhesive kinesiology or physio tape adapted to provide heating and cooling, said tape comprising:

a first layer of flexible high quality porous fabric;

a second layer of flexible high quality porous fabric;

plural pads of electrocaloric polymeric material mounted between the first and second layers of flexible high quality porous fabric, each pad including:
two layers of polarized electrocaloric polymer film and
a nanotube electrode mounted between said layers of polarized electrocaloric polymer film;

a controller, mounted on said tape, for electrically actuating said pads of electrocaloric material;

at least one of said layers of flexible high quality porous fabric including plural arrangements for retaining said plural pads and providing electrical connections thereto; and a bus mounted between the layers of porous material for providing electrical connection between the controller and the pads through said electrical connections.

* * * * *